(12) United States Patent
Brady

(10) Patent No.: US 6,540,754 B2
(45) Date of Patent: Apr. 1, 2003

(54) APPARATUS AND METHOD FOR MULTIPLY FOLDING AND INSERTING AN INTRAOCULAR LENS IN AN EYE

(75) Inventor: Daniel G. Brady, San Juan Capistrano, CA (US)

(73) Assignee: Advanced Medical Optics, Inc., Irvine, CA (US)

(*) Notice: Subject to any disclaimer, the term of this patent is extended or adjusted under 35 U.S.C. 154(b) by 0 days.

(21) Appl. No.: 09/770,867

(22) Filed: Jan. 26, 2001

(65) Prior Publication Data
US 2002/0103490 A1 Aug. 1, 2002

(51) Int. Cl.[7] .................................................. A61F 9/00
(52) U.S. Cl. ......................................................... 606/107
(58) Field of Search ................................ 606/107, 166, 606/170; 623/6.11, 6.12, 6.38

(56) References Cited

U.S. PATENT DOCUMENTS

| | | | | |
|---|---|---|---|---|
| 5,549,614 A | * | 8/1996 | Tunis | 606/107 |
| 5,702,402 A | * | 12/1997 | Brady | 606/107 |
| 5,711,317 A | * | 1/1998 | McDonald | 438/127 |
| 6,143,000 A | * | 11/2000 | Feingold | 606/107 |
| 6,206,887 B1 | * | 3/2001 | McDonald | 606/107 |

* cited by examiner

Primary Examiner—Ismael Izaguirre
(74) Attorney, Agent, or Firm—Stout, Uxa, Buyan & Mullins, LLP; Frank J. Uxa; Peter Jon Gluck

(57) ABSTRACT

An intraocular lens (IOL) insertion system, cartridge and/or combination cartridge and folding member that facilitates multiply folding an IOL within a load chamber of the cartridge prior to insertion in an eye. In the system embodiment, a folding member is provided in a handpiece that interacts with the cartridge to multiply fold the IOL therewithin. Alternatively, the cartridge may incorporate the folding member in its structure, or a separate folding member that interacts with the cartridge may be provided in a combination. The folding member may be a planar element that extends through a slot in the wall of the load chamber to displace a midportion of the IOL away from the inner wall of the load chamber. Desirably, the multiply folded configuration that results is an M-shape or a W-shape, depending on orientation. The cartridge may further include structure that retains the multiply folded configuration of the IOL as it passes through an injection tube and into the eye.

24 Claims, 5 Drawing Sheets

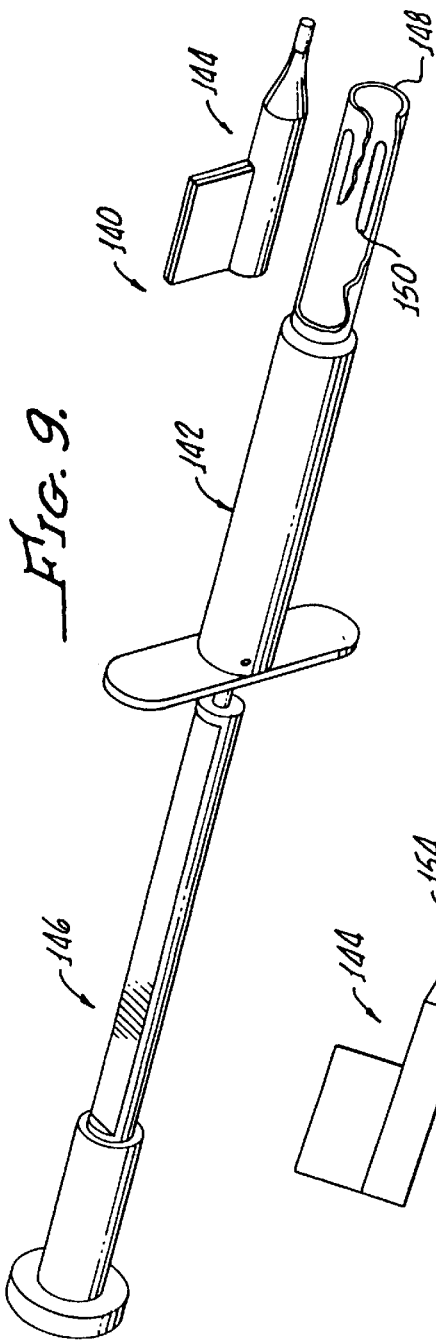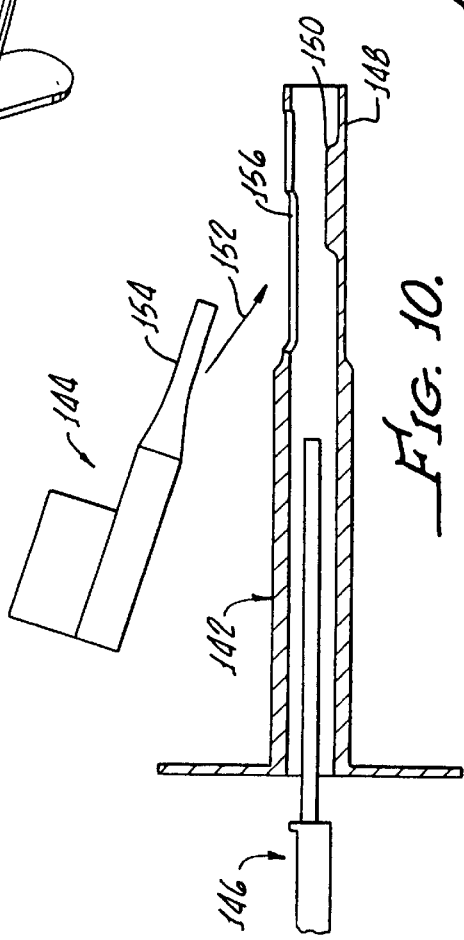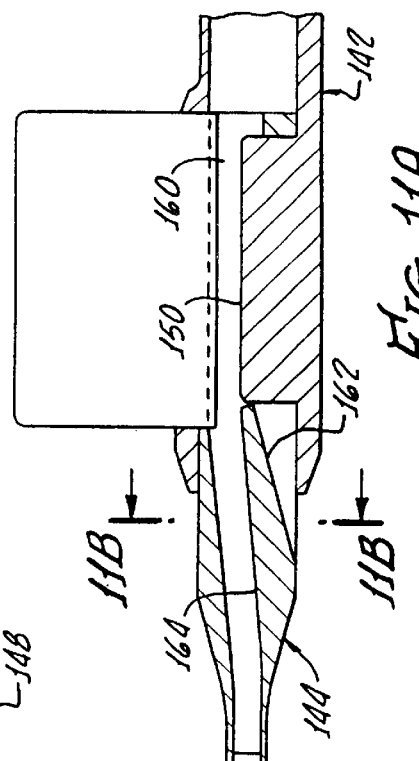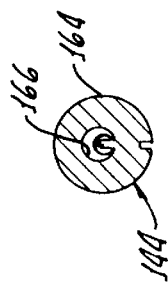

APPARATUS AND METHOD FOR MULTIPLY FOLDING AND INSERTING AN INTRAOCULAR LENS IN AN EYE

BACKGROUND OF THE INVENTION

The present invention relates to apparatus and methods for inserting an intraocular lens (IOL) through a small incision into an eye. More particularly, the invention relates to such apparatus and methods for first multiply folding an IOL to attain a reduced insertion profile and then inserting the lens through an incision in the eye.

An intraocular lens (IOL) is implanted in the eye, for example, as a replacement for the natural crystalline lens after cataract surgery or to alter the optical properties of (provide vision correction to) an eye in which the natural lens remains. IOLs often include an optic, and preferably at least one (and normally two) flexible fixation member or haptic, which extends from the optic and becomes affixed in the eye to secure the lens in position. The optic normally includes an optically clear lens.

The IOL preferably is implanted directly into the eye through a small incision formed in the ocular tissue of the eye. Making the incision as small as possible reduces trauma and speeds healing. To fit through this small incision, optics of modern IOLs are designed to be deformed, e.g., folded, rolled or the like, to a relatively small insertion profile and then allowed to substantially return to their original shape within the eye. To permit folding (deforming) so that the IOL can be inserted into the eye through a small incision, the optic may be made of silicone polymeric material, flexible or foldable acrylic polymeric material, and the like.

A very useful technique for inserting an IOL into the eye includes the use of an IOL injector or cartridge, such as the IOL injector described in Bartell, U.S. Pat. No. 4,681,102. These IOL injectors include a load chamber which is connected to an injection tube. The load chamber includes a lumen for receiving the IOL and is hinged so that the side walls thereof can be opened like a book. Closure of this lumen folds the IOL and maintains the IOL in a folded state. The injection tube includes a small diameter distal tip which is insertable into the incision within the eye. The IOL is transferable from the load chamber through the injection tube and into the eye. These IOL injectors simplify the placement of the IOL within the eye and reduce chances of surgeon error.

In these generally accepted apparatuses, the insertion cartridge is held in a handpiece having a plunger rod longitudinally displaceable therewithin. The plunger rod moves distally to urge the IOL from the load chamber through the injection tube and into the eye. Zaleski U.S. Pat. No. 5,643,276 discloses an IOL insertion apparatus in which the rod is rotated relative to the handpiece being held by the surgeon The rod, in turn, contacts the IOL and provides the IOL in the desired orientation for insertion into the eye. The disclosure of this patent is incorporated in its entirety herein by reference.

Many prior art cartridges singly fold the IOL into a rolled or U-shaped configuration. That is, two diametrically opposite side edges of the optic are folded toward one another into close or overlapping proximity. This rolled configuration reduces the insertion profile at least in one dimension from the optic diameter to about one half the optic diameter. Most currently available IOLs have a minimum diameter on the order of 6 mm and a minimum thickness of 1 mm to 2 mm. Most practical intraocular lens implantation procedures thus require an incision in the eye that is greater than 3–4 mm, to also accommodate the injection tube. It would be advantageous to provide IOL insertion apparatus and methods which reduce the insertion profile of a folded IOL in the apparatus, thus facilitating insertion of the IOL through a small incision in the eye and reducing trauma to the patient.

In addition, the IOL is inserted and unfolds in the anterior chamber of the eye to generally assume its final orientation. To accomplish this using a conventional U-shaped fold configuration, the IOL is maneuvered into an orientation in which the opposite side edges are posteriorly directed (to the rear), while the convex midportion of the optic is anteriorly directed (to the front). When released from the injection tube, therefore, the convex face of the optic is facing in the anterior direction, parallel and spaced from the cornea. To enable this desirable insertion/unfolding step, the space required in the anterior-posterior direction within the eye is on the order of 3 mm (about half the diameter of the optic). It would be desirably to be able to reduce the space necessary for the unfolding step, to help avoid contacting the IOL with surrounding anatomical structures.

An apparatus for further reducing the insertion profile of an IOL from the conventional U-shape can be seen in Brady, U.S. Pat. No. 5,702,402. In that patent, forceps manipulated in conjunction with a tubular member form a "W" configuration in an IOL with multiple folds, as seen for example, in FIGS. 2B and 10. McDonald, et al., U.S. Pat. No. 5,711,317, and McDonald, U.S. Pat. No. 5,919,197 both disclose folding of an IOL into an "M" shape (the same as the "W" shape) to reduce the insertion profile. The folding is carried out with a relatively complex five-fingered wire element. There is a need for a simpler and more reliable way to multiply fold IOLs to produce a smaller insertion profile.

SUMMARY OF THE INVENTION

The present invention provides an improved apparatus for inserting an intraocular lens through an incision into an eye. The apparatus operates in an environment that is similar to existing systems, with a cartridge being loaded into a handpiece, and plunger rod of the handpiece extending through a lumen in the cartridge to push an intraocular lens from an injection tube of the cartridge through an incision in the eye.

In one aspect, the present invention provides a system for multiply folding an intraocular lens having an optic prior to insertion of the lens in an eye. The system includes an insertion cartridge for receiving the intraocular lens in a singly folded configuration, and a folding member sized to pass through an aperture in the cartridge and multiply fold the lens. The insertion cartridge includes a generally cylindrical proximal loading chamber defining an axis and sized to receive the lens in its singly folded configuration with the optic being curved in a first direction and generally conforming to an inner wall of the chamber. Upon passage through the aperture in the cartridge, the folding member contacts a midportion of the optic and displaces it away from the inner wall, curving the optic in a second direction opposite the first direction.

The folding member may be formed separately or as part of the cartridge. If part of the cartridge, the folding member may be pivotally connected thereto so as to move radially with respect to the aperture. Locking structure may be provided to retain the folding member in its radially inward position. The aperture preferably comprises a closed-ended axial slot and a folding member is desirably axially elongate so as to fit and be guided through the slot and contact the optic generally along an axial line. The folding member may include a stop portion size larger than the aperture to limit the insertion depth of the folding member. The system may further include a handpiece for receiving the cartridge including a pusher rod for displacing the intraocular lens from within the cartridge into an eye. The folding member may therefore be formed as part of the handpiece, such as a fixed axial rib extending inward from an inner wall of a handpiece chamber that aligns with and extends through the axial slot in the cartridge.

In a further aspect of the present invention, an insertion cartridge for receiving and folding an intraocular lens having an optic comprises a generally cylindrical loading chamber defined by two arcuate walls. The arcuate walls are convertible between a closed relationship defining the loading chamber and an open relationship exposing the inner concave surfaces of the walls. An intraocular lens may be placed on the concave surfaces in the open relationship and may be singly folded by conversion of the arcuate walls to the closed relationship. The cartridge further includes an injection lumen contiguous with the loading chamber and extending distally therefrom. A closed-ended axial slot defined in the cartridge opens to the loading chamber in a location adjacent a midportion of the optic of the singly folded intraocular lens. The slot is sized to receive and axially elongate folding member therethrough that contacts and displaces the midportion of the optic radially inward, thereby multiply folding the intraocular lens into an "M" or "W" shape. The closed-ended axial slot of the cartridge may be located between the two arcuate walls, either at the hinge, or opposite the hinge between two free edges of the walls. A pair of folding wings may extend radially outward from the free edges of the arcuate walls, and the slot may be defined by facing recesses in the folding wings.

In another aspect of the present invention, a method of multiply folding an intraocular lens having an optic prior to insertion of the lens in an eye comprises the steps of placing the lens in a generally cylindrical loading chamber of cartridge, and inserting a folding member through an aperture in the cartridge. The lens is placed in the loading chamber such that the optic generally conforms to an inner wall of the cylindrical chamber and is singly curved in a first direction. The folding member contacts a midportion of the optic of the lens and displaces it away from inner wall, thus curving the optic in a second direction opposite first so that the lens is multiply folded within the loading chamber. The method may include providing a folding member separate from the cartridge, the folding member including a planar portion and a stop portion for limiting insertion of the planar portion through the aperture. Alternatively, a handpiece may be provided into which the cartridge is mounted, wherein the folding member is formed on the handpiece and inserts automatically through the aperture when the cartridge is mounted on the handpiece. The folding member may be fixed or movable on the handpiece. Still further, the folding member may be movably connected to the cartridge and displacing inward upon mounting of the cartridge on handpiece.

These and other aspects of the present invention will become apparent in the following detailed description and claims, particularly when considered in conjunction with the accompanying drawings in which like parts bear like reference numerals.

BRIEF DESCRIPTION OF THE DRAWINGS

FIG. 9 is a perspective exploded view of an IOL insertion system of the present invention having a handpiece and an insertion cartridge;

FIG. 10 is a partial sectional view of the insertion system of FIG. 9 prior to coupling the insertion cartridge with the handpiece;

FIG. 11A is a partial sectional view of the insertion system of FIG. 9 after coupling the insertion cartridge with the handpiece;

FIG. 11B is a transverse sectional view of the insertion cartridge taken along line 11B—11B of FIG. 11A;

DETAILED DESCRIPTION OF THE PREFERRED EMBODIMENTS

Figure 1:
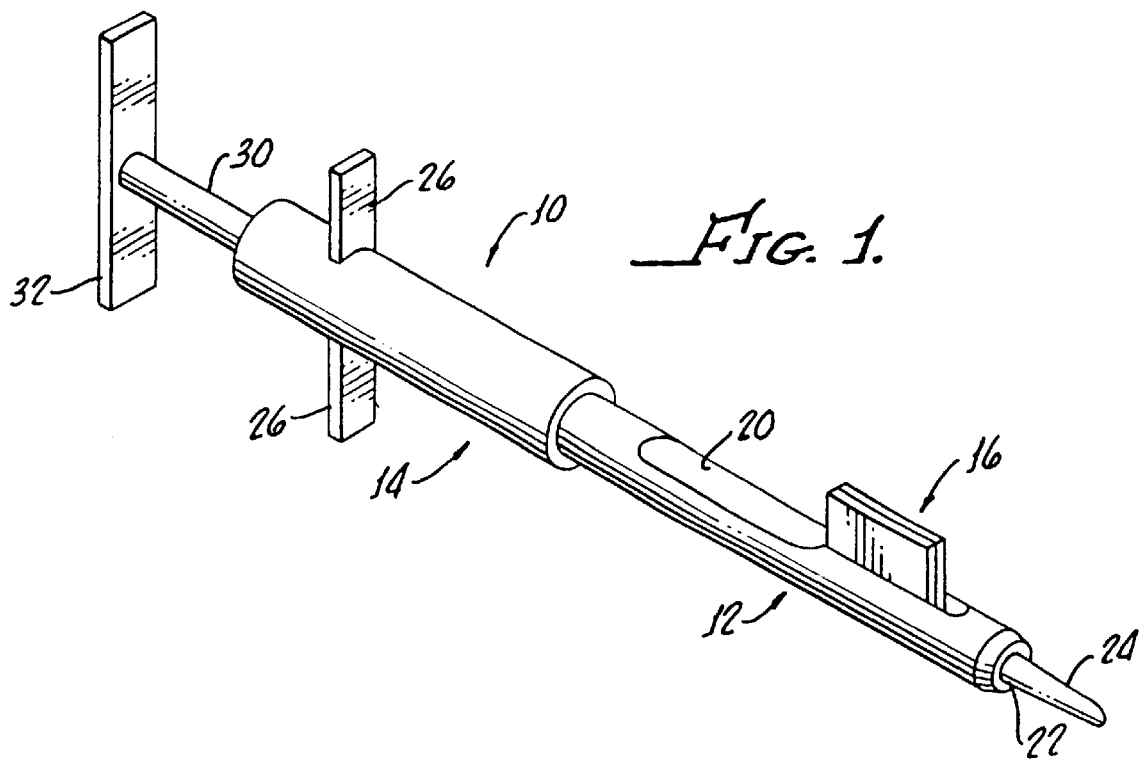
FIG. 1 is a perspective view of a general insertion apparatus of the present invention.

FIG. 1 illustrates an IOL insertion apparatus of the prior art, shown generally as 10, that generally functions like the apparatus of the present invention. The apparatus 10 comprises a proximal housing 12, a distal housing 14 and a folding cartridge 16. The folding cartridge 16 is similar to that shown in Bartell U.S. Pat. No. 4,681,102, and is typically known in the art as a Bartell-type folding cartridge. The cartridge 16 by itself singly folds or rolls the lens within. Proximal housing 12 is operatively coupled to distal housing 14 and includes a through opening 20 through which the folding cartridge 16 can be placed. Proximal housing 12 further includes a forward opening 22 through which the injection tube 24 of folding cartridge 16 extends distally. Distal housing 14 includes two oppositely disposed finger supports 26 which extend outwardly from the outer peripheral surface 28 of the distal housing.

Apparatus 10 also includes a plunger rod 30 which includes an enlarged proximal end 32 effective to push plunger rod 30 through distal housing 14, as will be discussed hereinafter.

Figure 2:
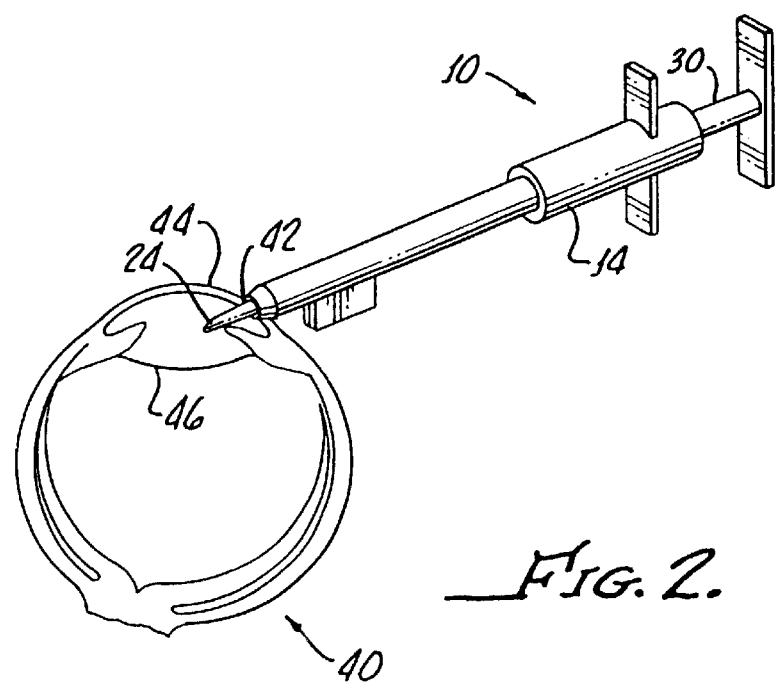
FIG. 2 is a schematic perspective drawing showing the placement of an insertion tube of the insertion apparatus of FIG. 1 in the eye.

With reference to FIG. 2, the IOL is to be placed in the eye 40 into an area formerly occupied by the natural lens of the eye. With the IOL in its folded position within apparatus 10, as described below, injection tube 24 is ready for insertion through an incision 42 in the sclera 44 of eye 40. Capsular bag 46 protects the posterior segment of the eye 40 and as one of the eye's constituent parts which is not injured by the insertion of the IOL with the injection tube 24 inserted within the eye 40 and the distal end properly positioned, the surgeon advances plunger rod 30 by manually pushing the plunger rod 30 relative to distal housing 14. This action moves IOL distally into injection tube 24. If needed, IOL can be repositioned in the eye by a small, bent needle or similar tool inserted into the same position.

FIG. 2 shows the sclera 44 having an incision through which the distal end portion of the injection tube 24 is passed. Alternately, the incision may be made through the cornea. Injection tube 24 preferably has a sufficiently small cross-section to pass into the eye 40 through an incision of about 3.5 mm or about 3.0 mm in the sclera 44. Once IOL is properly positioned in eye 40, and apparatus 10 is withdrawn from the eye, the incision in the sclera may be closed, for example, using conventional techniques. After use, folding cartridge 13, which is made of a polymeric material, such as polypropylene, preferably is disposed of. Remaining portions of apparatus 10, which preferably are made of metal, such as surgical grade stainless steel, may be reused after sterilization and disinfection. Any suitable material or materials of construction may be employed in the various components of the apparatus in accordance with the present invention.

The present invention provides a number of insertion cartridges, combination cartridges and folding members, and combination cartridges and insertion system handpieces that function to multiply fold IOLs and produce a smaller insertion profile. The preferred multiply folded configuration illustrated herein is either "M-shaped" (or "W-shaped," if you will) with essentially three folds. Of course, the apparatuses and methods of the present invention may be used to produce other multiply folded IOL configurations, with four or more folds, for example. Furthermore, the preferred environment for multiply folding IOLs is within a hinged Bartell-type folding cartridge. However, other insertion cartridges such as non-hinged tubes may be adapted in accordance with the principles of the present invention. Therefore, the reader will appreciate that the invention is not strictly limited by the embodiments shown and described herein.

FIGS. 3, 4A–4B, and 5A–5B illustrate a first exemplary IOL insertion cartridge 50 and separate folding member 52 that, used in conjunction, simply and reliably fold an IOL within the cartridge into an M-shape. The cartridge 50 is similar to that described above with reference to FIGS. 1 and 2, and includes a proximal generally tubular body 54 having a pair of hinged arcuate walls 56a, 56b along a proximal portion, and a distal injection tube 58. The injection tube 58 defines a gradually narrowing injection lumen 60 therewithin that terminates in a distal mouth 62.

Figure 4A:
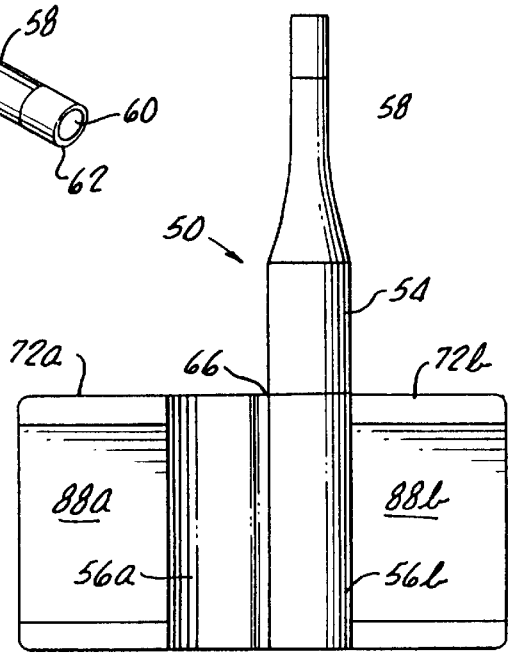
FIGS. 4A and 4B are plan and elevational views, respectively, of the cartridge of FIG. 3 with a pair of folding wings opened up.
Figure 4B:
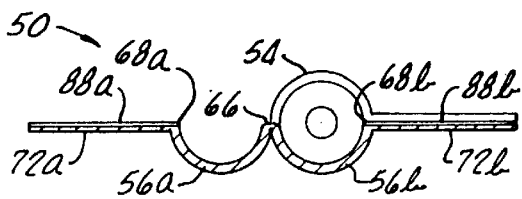
Figure 6:
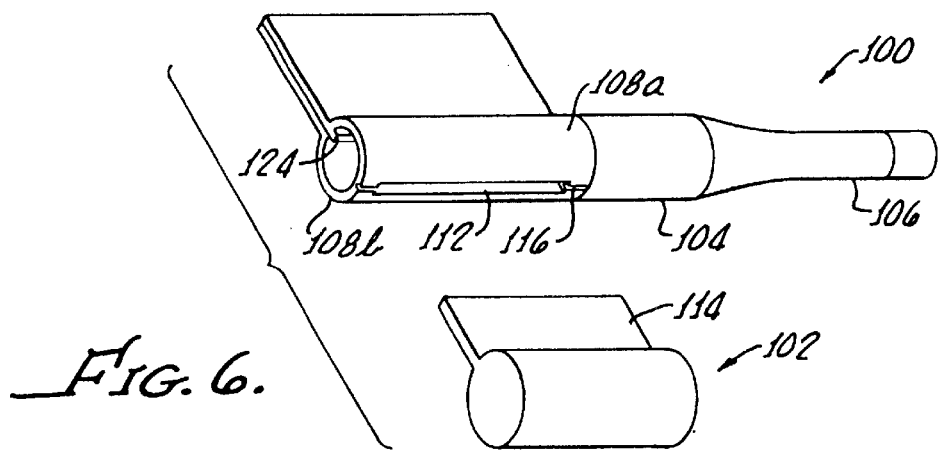
FIG. 6 is a perspective exploded view of a second exemplary IOL insertion cartridge and folding member of the present invention.
Figure 7A:
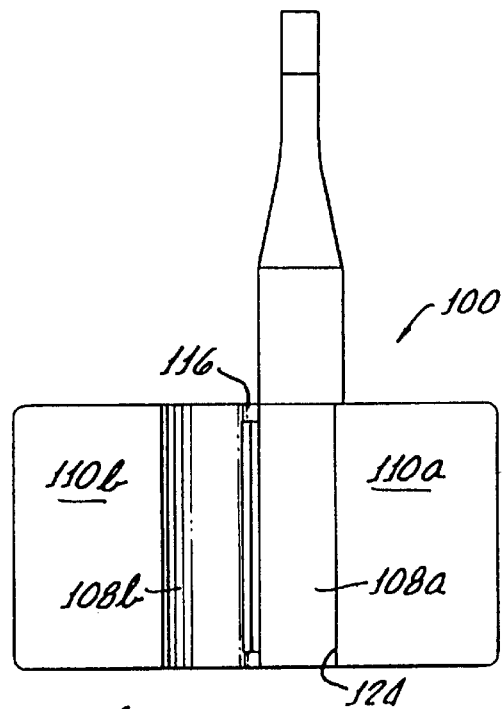
FIGS. 7A and 7B are plan and elevational views, respectively, of the cartridge of FIG. 6 with a pair of folding wings opened up.
Figure 7B:
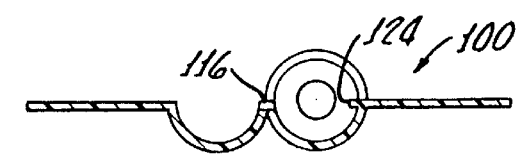

With reference to FIGS. 4A and 4B, each arcuate wall 56a, 56b has a fixed edge coincident with an axial hinge 66, and a free edge 68a, 68b. One of the arcuate walls 56b is fixed with respect to the tubular body 54, while the other wall 56a pivots about the hinge 66 with respect thereto, and with respect to the remainder of the cartridge 50. The arcuate walls 56a, 56b are seen in an open configuration in FIGS. 4A–4B, and in a closed configuration in FIGS. 5A–5B defining a generally cylindrical load chamber 70 therewithin. A planar folding wing 72a, 72b extends generally radially outward from each respective free edge 68a, 68b.

The injection lumen 60 extends generally axially contiguous with the cylindrical load chamber 70 that is defined within the closed arcuate walls 56a, 56b. An IOL 74 is seen positioned within the load chamber 70 in FIG. 5A in a singly folded, generally upside-down horseshoe- or U-shape. It should be understood that the portion of the IOL 74 that is seen is the optic, with the fixation members not shown but extending both distally and proximally, into and out of the page, respectively. The upside-down U-shape configuration occurs automatically when no bracing ribs or other structure within the load chamber is provided to hold the IOL 74 from rotation. In this configuration, the optic of the IOL 74 has a pair of side edges 76a, 76b folded toward one another, and a midportion 78 curved in a first direction in conformity with the concave inner surfaces of the arcuate walls 56a, 56b.

Figure 3:
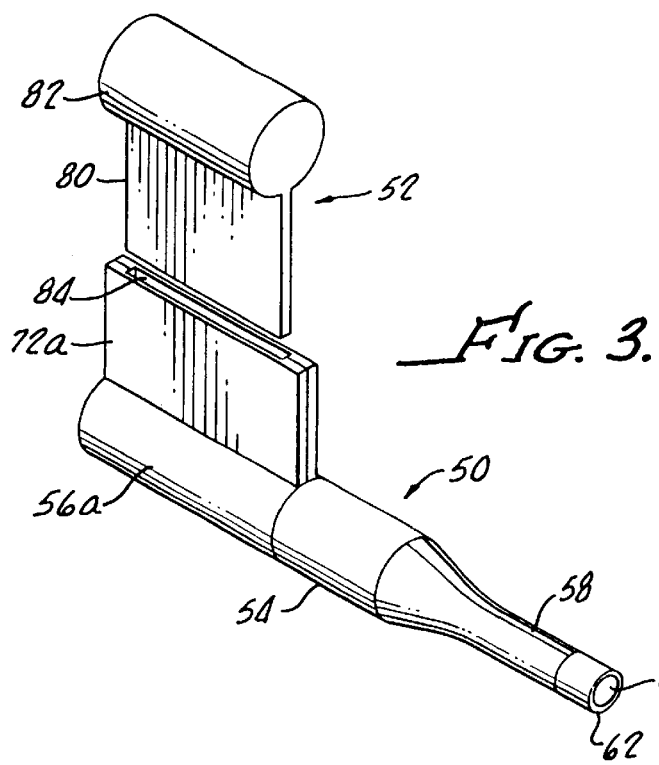
FIG. 3 is a perspective exploded view of a first exemplary IOL insertion cartridge and folding member of the present invention.
Figures 5A, 5B:
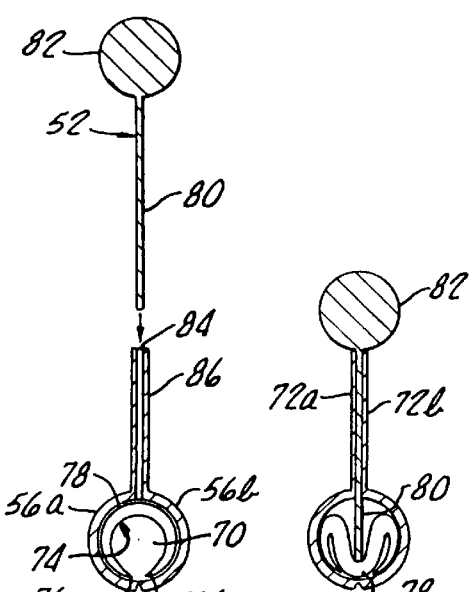
FIGS. 5A and 5B show an IOL folding operation of the present invention using the folding member and cartridge of FIG. 3.

The folding member 52 seen in FIG. 3, and also in FIGS. 5A–5B, comprises an elongate planar portion 80 and a stop portion 82; which latter element in an exemplary form is a cylinder. The planar portion 80 is a slim panel or board-like member sized to closely fit through a closed-ended slot 84 and into a passageway 86 (FIG. 5A) defined between the folding wings 72a, 72b. The slot 84 and passageway 86 are formed by a pair of rectangular recesses 88a, 88b on the interior faces of the folding wings 72a, 72b. The portions of the interior faces of the folding wings 72a, 72b that are not recessed contact each other in the closed configuration of the cartridge 50.

As seen in FIG. 5B, the planar portion 80 has a length that extends through the passageway 86 and into the load chamber 70 to multiply fold or deform the IOL 74. Specifically, the planar portion 80 contacts the midportion 78 of the optic of the IOL 74 and displaces it away from the inner surfaces of the arcuate walls 74a, 74b. The midportion 78 thus curves in a second direction opposite its first direction of curvature conforming to the inner surfaces of the arcuate walls 74a, 74b. In the illustrated embodiment, with the folding wings 72a, 72b projecting upward, the resulting multiply folded configuration of the IOL 74 is an M-shape. The stop portion 82 of the folding member 52 limits insertion of the planar portion 80, and thus limits the extent to which the IOL 74 is multiply folded. The closed-ended slot 84 and passageway 86 provide a guide for insertion of the planar portion 80 into the load chamber 70. In this context, visual or physical markers aligned with the slot 84 within the load chamber 70 may be provided to aid in proper positioning of the IOL 74. Further, it should be noted that only a single slot on one side of the load chamber 70 is needed for entry of the folding member 52 to complete the multiple folding of the IOL.

Preferably, the planar portion 80 extends far enough such that the IOL 74 retains the M-shape as shown upon removal of the folding member 52. That is, the midportion 78 of the IOL 74 may possess a bi-stable resilient character between the upside-down U-shape of FIG. 5A, and the M-shape of FIG. 5B. Causing the midportion 78 to bow downward as seen in FIG. 5B may cause the IOL 74 to retain that shape. Much depends on the IOL material, however, and structure may be optionally provided as described below to maintain the multiply folded IOL configuration. The IOL 74 is subsequently urged from within the load chamber 70 through the injection lumen 60 and out of the mouth 62. As the IOL 74 progresses distally through the injection lumen 60 it is constricted into an even smaller multiply folded size for passage through the mouth 62 and incision in the eye.

FIGS. 6, 7A–7B, and 8A–8B illustrate a second embodiment of an exemplary IOL insertion cartridge 100 and separate folding member 102 that, used in conjunction, simply and reliably fold an IOL within the cartridge into an M-shape. As before, the cartridge 100 includes a generally tubular body 104 and a co-linear injection tube 106. The arcuate walls 108a, 108b and associated folding wings 110a, 110b are similar to those described above, except that a closed-ended slot 112 for receiving a planar portion 114 of the folding member 102 is located in the region of the hinge 116. Specifically, as seen best in FIGS. 6 and 7A, the hinge 116 is discontinuous with two relatively short hinge portions defining the ends of the elongate slot 112.

Figure 8A:
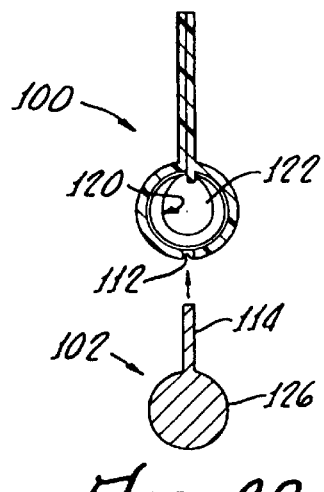
FIGS. 8A and 8B show an IOL folding operation of the present invention using the folding member and cartridge of FIG. 6.
Figure 8B:
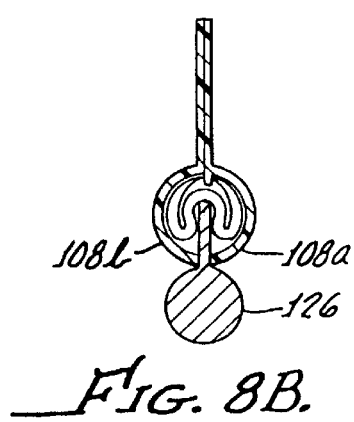

As seen in FIGS. 8A–8B, the planar portion 114 of the folding member 102 has a length sufficient to fit through the slot and multiply fold an IOL 120 within a load chamber 122 of the cartridge 100. In this embodiment, the IOL 120 initially assumes a U-shape by virtue of a retaining rib 124 extending inward to the load chamber 122. That is, as seen in FIG. 72, the retaining rib 124 temporarily secures one edge of the IOL 120 during loading and prevents it from freely rotating into an upside-down U-shape when the arcuate walls 108a, 108b are folded together.

The folding member 102 fully inserts through the slot 112 until a stop portion 126 contacts the exterior of the cartridge 100. In the orientation of FIG. 8B, therefore, the IOL 120 assumes a substantially W-shape. Again, optional structure to retain the IOL 120 in this multiply folded configuration may be required, depending on the material of the IOL.

FIGS. 9 and 10 illustrate an IOL insertion system 140 of the present invention including a handpiece 142 for receiving a folding Bartell-type IOL insertion cartridge 144, and a plunger 146 adapted to linearly translate within the handpiece. Various configurations of handpieces 142 and plungers 146 are known, and may be used in the context of the present invention. The handpiece 142 includes a distal tubular portion 148 for receiving the cartridge 144.

As seen cut away in FIG. 9, and in section in FIG. 10, a folding member 150 is provided on an inner wall of the tubular portion 148. In an exemplary embodiment, the folding member 150 comprises a fixed axially-extending rib projecting radially inward from the inner wall of the tubular portion 148. As will be described below, the folding member 150 is sized to fit within a slot (not shown) formed within the hinge region of the folding cartridge 144. The folding member 150 thus extends within the load chamber of cartridge 154 to multiply fold the IOL therewithin.

With reference to FIG. 10, the insertion cartridge 144 is shown just prior to coupling with the handpiece 142 in the direction of arrow 152. The injection tube 154 of the cartridge 144 extends through an elongate opening 156 in the distal tubular portion 148, and projects from the distal end thereof as seen in FIG. 11A. To ensure the proper multiple folding operation, the IOL (not shown) is positioned within the load chamber 160 (FIG. 11A) of the cartridge 144, in the same manner as seen in FIG. 8A; that is, in a U-shape with the side edges projecting toward the folding wings of the cartridge. Upon coupling of the cartridge 144 with the handpiece 142, the folding member 150 extends through the aforementioned slot in the hinge region, in the same manner as does the planar portion 114 of the folding member 102 of FIG. 8B. Projection of the folding member 150 into the load chamber 160 displaces the midportion of the optic of the IOL toward the folding wings, thus multiply folding the IOL into the W-shape as seen in FIG. 8B. To facilitate entry of the fixed folding member 150 through the slots of the cartridge 144, a short ramped recess 162 may be formed in the underside of the tubular body of the cartridge leading to the slot.

FIG. 11A illustrates a further aspect of the present invention to ensure that the multiply folded IOL maintains its shape through the injection tube 154. This may be particularly important when certain materials for the IOL are used, such as silicone, and relatively less important when other materials such as acrylic are used. Specifically, a tapered rib 164 projects inwardly to the injection lumen 166 and extends distally from a location that is adjacent the load chamber 160 to a location at which the injection lumen 166 has narrowed to a sufficient degree to compress and retain the multiply folded IOL configuration. The relative projected sized of the tapered rib 164 within the injection lumen 166 is seen in FIG. 11B. As the IOL is urged distally from the load chamber, the tapered rib 164 is aligned with and takes over from the folding member 150 to maintain the W-shape of the IOL. As the injection lumen 166 reduces in size, the tapered rib 164 also gradually reduces in height until it disappears.

The IOL insertion system of FIGS. 9–11 incorporates a fixed folding member into the handpiece which interacts with the insertion cartridge as it is coupled with the handpiece. Alternatively, a movable folding member associated with the handpiece may be provided that is displaced from a retracted position to an operable position extending through a slot in the cartridge. For example, the folding member 150 as seen in FIG. 9 may be radially displaceable with respect to the tubular portion 148. The cartridge 144 is thus first coupled to the handpiece 142 with the folding member 150 in a retracted position. Subsequently, the movable folding member 150 is displaced radially inward through the slot in the cartridge 144 so as to multiply fold the IOL therewithin. Those of skill in the art will understand that there are multiple variations of either fixed or movable folding members associated with the handpiece that interact with the cartridge either as the cartridge is coupled with the handpiece, or subsequently.

Figure 12:
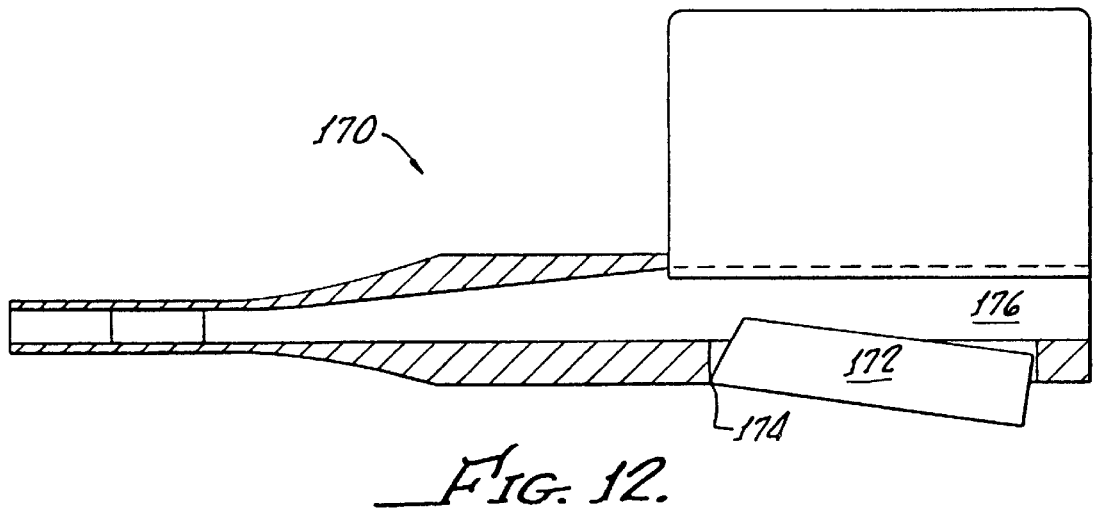
FIG. 12 is a sectional view through an alternative insertion cartridge of the present invention having a movable folding member associated therewith.

In a still further embodiment, as seen in FIG. 12, a movable folding member may be incorporated into the structure of an insertion cartridge 170. In the illustrated embodiment, the movable folding member 172 comprises an elongate finger that is hinged at 174 to one side wall of the load chamber 176 so as to pivot radially thereabout. The folding member 172 is shown in a retracted configuration, and is subsequently cammed radially inward to the load chamber 176 upon coupling of the cartridge 170 with the associated handpiece. As before, the IOL must be positioned as seen in FIG. 8A such that inward movement of the folding member 172 multiply folds the IOL into the W-shape of FIG. 8B. Again, numerous variations of movable folding members associated with the cartridge are contemplated other than the specific embodiment illustrated in FIG. 12. For example, the folding member may be constrained to linearly translate in a channel as opposed to pivoting.

Figure 13:
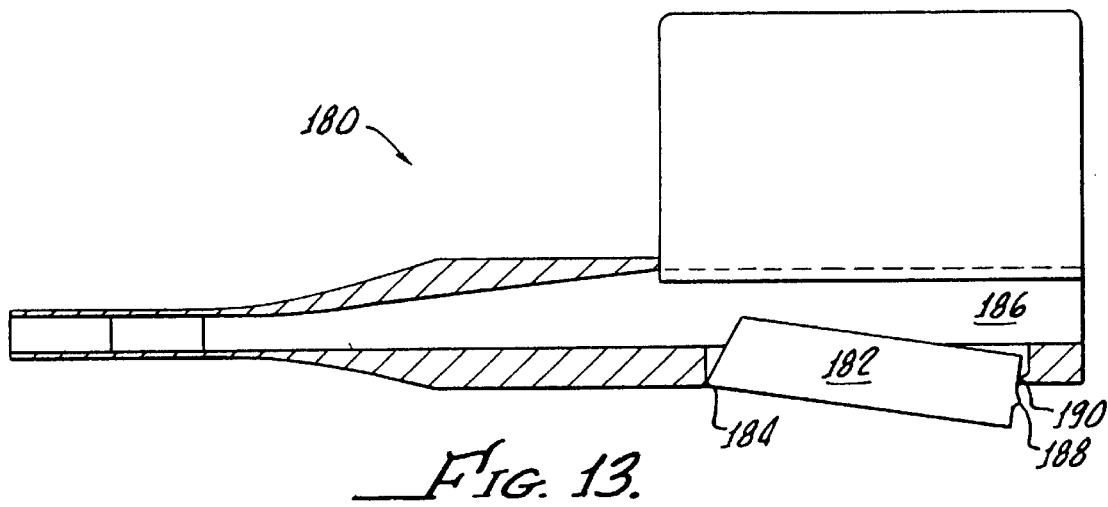
FIG. 13 is a sectional view through a still further alternative insertion cartridge of the present invention having a movable and lockable folding member associated therewith.

In another alterative configuration seen in FIG. 13 a movable and lockable folding member is incorporated into the structure of an insertion cartridge 180. The movable folding member 182 is similar to that described and shown with respect to FIG. 12, and comprises an elongate finger that is hinged at 184 to one side wall of the load chamber 186 so as to pivot radially thereabout. A projection or tooth 188 on the moving end of the folding member 182 interacts with a lip 190 on the cartridge 180 to lock the folding member in its radially inward position. The folding member 182 is shown in a retracted configuration, and may be displaced radially inward to the load chamber 186 upon coupling of the cartridge 170 with the associated handpiece. Alternatively, the folding member 182 may be displaced radially inward to the load chamber 186 prior to coupling with the handpiece to ensure proper multiple folding of the IOL during handling of the cartridge. Other locking structure such as ratchets, ball detents, etc. may be used.

While this invention has been described with respect of various specific examples and embodiments, it is to be understood that the invention is not limited thereto and that it can be variously practiced within the scope of the following claims.

What is claimed is:

1. A system for multiply folding an intraocular lens having an optic prior to the insertion in an eye, comprising:
   an insertion cartridge having a generally cylindrical proximal loading chamber defining an axis therethrough, the loading chamber being sized to receive an intraocular lens in a singly folded configuration wherein the optic generally conforms to an inner wall of the cylindrical chamber and is curved in a first direction; and
   a folding member sized to pass through an aperture in the cartridge opening to the loading chamber, the folding member contacting a midportion of the optic and having sufficient length to displace the midportion away from the inner wall and curve the optic in a second direction opposite the first direction so that the intraocular lens is multiply folded within the loading chamber.

2. The system of claim 1, wherein the folding member is formed as part of the cartridge.

3. The system of claim 2, wherein the folding member is pivotally connected to the cartridge so as to move radially with respect to the aperture.

4. The system of claim 3, further including locking structure to retain the folding member in a radially inward position with respect to the aperture.

5. The system of claim 1, wherein the folding member is formed separately from the cartridge.

6. The system of claim 5, wherein the aperture comprises a closed-ended axial slot and the folding member is axially elongate so as to fit and be guided through the slot and contact the optic generally along an axial line.

7. The system of claim 6, wherein the folding member comprises a planar portion sized to fit through the slot.

8. The system of claim 7, wherein the folding member further comprises a stop portion sized larger than the slot to limit the insertion depth of the planar portion through the slot.

9. The system of claim 1, further including a handpiece for receiving the cartridge including a pusher rod for displacing the intraocular lens from within the cartridge into an eye, wherein the folding member is formed as part of the handpiece.

10. The system of claim 9, wherein the folding member comprises an axial rib projecting inwardly from an inner wall of a cartridge receiving chamber of the handpiece, and wherein the aperture comprises an axial slot sized to receive the rib, the rib entering the slot when the cartridge is received by the handpiece.

11. An insertion cartridge for receiving and folding an intraocular lens having an optic, the cartridge comprising:
   a generally cylindrical loading chamber defined by two arcuate walls of the cartridge, the two arcuate walls being convertible between a closed relationship defining the loading chamber and an open relationship exposing the inner concave surfaces, wherein an intraocular lens placed on the concave surfaces in the open relationship may be singly folded by conversion of the arcuate walls to the closed relationship;
   an injection lumen contiguous with the loading chamber and extending distally therefrom; and
   a closed-ended axial slot defined in the cartridge and opening to the loading chamber in a location adjacent a midportion of the optic of the singly folded intraocular lens therein, the slot being sized to receive an axially elongate folding member therethrough that contacts and displaces the midportion of the optic radially inward thereby multiply folding the intraocular lens into an "M" or "W" shape.

12. The cartridge of claim 11, wherein the two arcuate walls are pivotally connected together at a hinge located between adjacent edges thereof, two free edges of the arcuate walls being thus adapted to move toward and away from one another, and wherein the axial slot is defined between the two arcuate walls.

13. The cartridge of claim 12, wherein the axial slot is located at the hinge.

14. The cartridge of claim 12, the axial slot is located in the loading chamber opposite the hinge and between the two free edges.

15. The cartridge of claim 14, further including a pair of folding wings extending generally radially from each respective free edge of the arcuate walls, wherein the axial slot is defined between the folding wings.

16. The cartridge of claim 11, wherein the cartridge further includes a moveable folding member connected to the cartridge and adapted to pass radially inward through the axial slot.

17. The cartridge of claim 16, wherein the moveable folding member is pivotally connected to the cartridge.

18. The cartridge of claim 16, further including locking structure to retain the folding member in a radially inward position with respect to the axial slot.

19. A method of multiply folding an intraocular lens having an optic prior to insertion in an eye, comprising:
   placing the intraocular lens in a generally cylindrical loading chamber of a cartridge such that the optic generally conforms to an inner wall of the cylindrical chamber and is singly curved in a first direction; and
   inserting a folding member through an aperture in the cartridge into contact with a midportion of the optic of the intraocular lens thus displacing the midportion away from the inner wall and curving the optic in a second direction opposite first so that the intraocular lens is multiply folded within the loading chamber.

20. The method of claim 19, further including providing a folding member separate from the cartridge, and wherein the step of inserting comprises inserting the folding member radially inward through the aperture.

21. The method of claim 20, wherein the folding member includes a planar portion and a stop portion, and the step of inserting includes fully inserting the planar portion into the aperture until the stop portion contacts the exterior of the cartridge.

22. The method of claim 19, further including providing a handpiece into which the cartridge is mounted and a plunger rod operatively coupled to the handpiece for displacing the intraocular lens through the cartridge into an eye, wherein the folding member is formed on the handpiece, the step of inserting automatically occurring upon mounting of the cartridge into the handpiece.

23. The method of claim 19, further including providing a handpiece into which the cartridge is mounted and a plunger rod operatively coupled to the handpiece for displacing the intraocular lens through the cartridge into an eye, wherein the folding member is movably associated with the handpiece, the step of inserting comprising displacing the folding member radially inward after mounting of the cartridge into the handpiece.

24. The method of claim 19, further including providing a handpiece into which the cartridge is mounted and a plunger rod operatively coupled to the handpiece for displacing the intraocular lens through the cartridge into an eye, wherein the folding member is movably formed on the cartridge, the step of inserting automatically occurring upon mounting of the cartridge into the handpiece.

* * * * *